United States Patent [19]

Koslo et al.

[11] Patent Number: 4,853,216

[45] Date of Patent: Aug. 1, 1989

[54] PROCESS AND COMPOSITION FOR THE TOPICAL APPLICATION OF ALPHA$_1$ ADRENERGIC AGONIST FOR PILOMOTOR EFFECTS

[75] Inventors: Randy J. Koslo, East Windsor; Alison B. Lukacsko, Robbinsville, both of N.J.

[73] Assignee: Bristol-Myers Company, New York, N.Y.

[21] Appl. No.: 33,987

[22] Filed: Apr. 2, 1987

[51] Int. Cl.$^4$ ............................................. D61K 7/15
[52] U.S. Cl. .................................... 424/73; 514/930
[58] Field of Search ................ 424/62, 70, 73; 8/405, 8/431, 550, 94.16, 161; 564/358, 363, 364, 365, 389, 390; 514/653, 654, 655, 930

[56] References Cited

U.S. PATENT DOCUMENTS

| | | | |
|---|---|---|---|
| 1,932,347 | 10/1933 | Legerlotz | 564/358 |
| 1,954,389 | 4/1934 | Legerlotz | 564/389 X |
| 2,359,707 | 10/1944 | Baltey et al. | 564/358 |
| 3,190,802 | 6/1965 | Zeile et al. | 424/73 |
| 3,296,076 | 1/1967 | Thomä | 424/73 |
| 3,296,077 | 1/1967 | Berg | 424/73 |
| 4,108,982 | 8/1978 | Amschler | 424/73 |
| 4,457,912 | 7/1984 | Scodari | 424/73 |

FOREIGN PATENT DOCUMENTS

| | | | |
|---|---|---|---|
| 1032482 | 6/1958 | Fed. Rep. of Germany | 424/73 |
| 943943 | 12/1963 | United Kingdom | 424/73 |

OTHER PUBLICATIONS

Cardiovascular Pharmacology, Michael J. Antonaccio, PhD. Editor, Raven Press Books, Ltd. NY 1977, pp. 340–341.
Drugs for Heart Disease, John Hamer Editor, Chapman and Hall Ltd. 1979, Chapter 5, pp. 322–343.
Webster's Third New International Dictionary of the English Language, Unabridged G.C. Merriam Co., MA 1966.
Stephens, Drug–Induced Piloerection in Man: A α–1 Adrenoceptor Against Effect; Hirman Toxicol., 5:319–324 (1986).

*Primary Examiner*—Ellis P. Robinson
*Assistant Examiner*—Susan S. Rucker
*Attorney, Agent, or Firm*—Morton S. Simon

[57] ABSTRACT

Processes and Compositions for effecting a pilomotor effect on a hair-bearing skin area by the application of an alpha$_1$ adrenergic agonist having essentially only alpha$_1$ adrenergic agonist activity.

25 Claims, No Drawings

PROCESS AND COMPOSITION FOR THE TOPICAL APPLICATION OF ALPHA$_1$ ADRENERGIC AGONIST FOR PILOMOTOR EFFECTS

This invention relates to processes and compositions for the topical application of a pilomotor effective amount of an alpha$_1$ adrenergic receptor stimulant which has essentially only alpha$_1$ activity to a hair-bearing skin area. More particularly it relates to processes and compositions of the aforementioned type that are concerned with treatment of hair-bearing skin areas in humans and which have as their purpose the erection of the hair on said hair-bearing areas to facilitate the physical or chemical handling of said hair. The processes and compositions of this invention have a wide variety of applications such as in conjunction with depilatory waxes, chemical depilatories, bleach creams and hair dyes. They have particular application in conjunction with shaving processes and compositions. To simplify the description of this invention the emphasis will be placed on its application to such shaving processes and composition as exemplary of the broader concept described above.

The processes and compositions of this invention can be applied to any of a variety of hair-bearing skin areas. When used in conjunction with shaving processes or compositions, application can be to the legs, axillary vaults, facial skin, etc. of the subject. When used in conjunction with bleach creams or hair dyes application may also be to hair bearing areas of the head and extremities.

Shaving facial hair is a chore that millions of men face on a daily basis and any assistance in making this process more comfortable and efficient would be welcome. Three criteria are generally recognized as necessary to provide the required shaving comfort and efficiency. These are (a) smoother shave, (b) closer shave and (c) reduced bleeding from razor cuts.

It has now been found that these criteria can generally be met by employing during the shaving process an alpha$_1$ adrenergic receptor stimulant which has essentially only alpha$_1$ activity. This can be applied as a pretreatment prior to the actual shaving operation or, as will be described in more detail below, may be incorporated in a shaving composition, e.g. shaving cream.

As is known in the pharmacology art, adrenergic receptors of two general types have been identified i.e. alpha and beta adrenergic receptors. In more recent times it has been recognized that the alpha adrenergic receptors do not form a homogeneous group. The are, in fact, two distinctly different subtypes that are identified as alpha$_1$ and alpha$_2$ adrenergic receptors. Stimulation of these receptors results in physiologically distinct effects even though these receptors may be situated in the same organ. Drugs which are known to stimulate these receptors are known as stimulants or agonists. Thus, for example, the drugs useful in the practice of the present invention are known as alpha$_1$ adrenergic receptor stimulants or alpha$_1$ adrenergic receptor agonists.

There have been suggestions in the prior art to incorporate in shaving preparation agents which have a pilomotor effect. In this regard attention is invited to U.S. Pat. Nos. 3,296,076, 3,296,077 and 3,190,802. The drugs described for use in these references are primarily alpha$_2$ adrenergic receptor agonists that have very little, if any, alpha$_1$ adrenergic receptor agonist activity. Moreover, they have various disadvantages that are not found in the use of the alpha$_1$ adrenergic receptor agonists employed in this invention. Thus, for example, some of the prior art materials are readily absorbed into the blood stream from a topical application thus introducing a hazard factor in their use. Furthermore, some of the materials are known to be long lasting and their activity would persist long after the shave is over. This also presents a hazard that is not found in the use of the alpha$_1$ adrenergic receptor agonists of the present invention. Other materials suggested for use in these references are known to cause nausea and vomiting, features absent in the materials employed in the present invention.

It is also taught in the prior art that subcutaneous injections of phenylephrine into the forearm causes localized piloerection. In this connection attention is invited to an article by G. W. Kortin and K. F. Rasp in, Arzneimittel Forschung 4:63–63, 1954, and entitled "The Pharmacology of The Experimental Pilomotor Reaction and the Local Influencing Thereof". As will be demonstrated in more detail below, the action of topically applied phenylephrine on facial pilomotor muscles and, as is characteristics of the present invention, was unexpected and therefore unobvious.

It is theorized that the closer and smoother shaves obtained by the processes and compositions of this invention are, to a large degree, due to the pilomotor muscle response that accompanies the application of the alpha$_1$ adrenergic receptor agonists to the hair bearing skin that is to be shaved. The hair is caused to stand up whereby it possible to cut the hair more readily and at a level closer to the skin. In addition the alpha$_1$ agonists employed in this invention also produce vasoconstriction that can reduce the bleeding associated with razor cuts which occur during the shaving process. The latter eliminates the need for the use of a styptic pencil which contains an irritating substance as its active ingredient.

The alpha$_1$ adrenergic receptor agonists that may be used in the practice of the present invention can be quite varied. All that is required is that their activity is be primarily only that which is associated with the alpha$_1$ activity. In other words they should exhibit no or practically no alpha$_2$ adrenergic receptor agonist action. Examples of the alpha$_1$ agonists which may be employed in the processes or compositions of this invention include, phenylephrine, methoxamine, etc. The alpha$_1$ agonist of choice for use in this invention is phenylephrine.

Phenylepherine has a more rapid onset of effect and shorter duration of action than pilomotor agents used in prior art shaving compositions. Prior art pilomotor agents, unlike phenylephrine, can be irritating and have some unwanted effects on the central nervous system. Phenylephrine and other alpha$_1$ adrenergic receptor agonists have a more limited spectrum of activity and thus less toxic potential because they affect only the alpha$_1$ receptors.

As indicated above, the alpha$_1$ receptor agonists may be employed in a composition used as a pre-treatment agent prior to shaving or may be directly incorporated in the shaving composition. In each instance the alpha$_1$ receptor agonists will be present in a sufficient concentration to elicit a pilomotor effect when applied to hair-bearing skin. This concentration may vary somewhat for different agonists. Generally, however, the alpha$_1$ agonist will be present in the range of from about 0.1% to about 10.0% by weight, based on the total weight of the composition in which it is contained, with the preferred range being from about 0.2% to about 2.0%, on the same weight basis.

When used in a pre-treatment composition, the nature of the ingredients (with the exception of the $alpha_1$ receptor agonist) contained in such composition can vary considerably. Usually, the $alpha_1$ agonists will be distributed in a liquid carrier. By way of illustration, such liquid carriers may comprise: (a) water or any aqueous solution containing organic or inorganic materials, e.g. saline or (b) organic solvents e.g. ethyl alcohol. In addition to said liquid carriers the pre-treatment compositions may also contain any ingredient which may modify or enhance the texture, appearance, scent, performance or chemical and physical stability. To illustrate this, the following may be mentioned:
1. Lubricants, e.g. silicones and isopropyl myristrate
2. Astringents, e.g. lactic acid and zinc phenolsulfonate
3. Fragrances, e.g. bay oil, rose water, orange oil, myrrh, and musk.
4. Medicinals and antiseptics, e.g. menthol and camphor.
5. Emollients, e.g. glycerol and sorbitols.
6. Preservatives, e.g. ascorbic acid and tocopherols.

For additional ingredients that may be included in the pre-treatment compositions of this invention mentioned is made to the following citation that is incorporated herein by way of reference: Bell, S.A. 1972. Preshave and Aftershave Preparations Pg. 13–37. In M. S. Balsam and E. Sagarin eds. 2 Vol. Cosmetics: *Science and Technology*. Wiley Interscience, New York.

When used as part of a shaving composition the remainder of the composition (apart from the $alpha_1$ adrengergic receptor) can be quite conventional but varied. These can serve to modify or enhance the texture, appearance, scent, performance or chemical and physical stability of the composition. Thus, in addition to the $alpha_1$ agonist the shaving composition may contain the following ingredients:
1. Carriers
   (a) Water or any aqueous solution containing organic or inorganic materials, e.g. distilled water.
   (b) organic solvents, e.g. ethyl alcohol
2. Lubricants, e.g. silicones, isopropyl myristate
3. Surfactants, e.g. nonionic, cationic, anionic or amphoteric surfactants.
4. Fragrances, e.g. bay oil, rose water, orange oil, myrrh, and musk.
5. Medicinals and antiseptics e.g. menthol and camphor.
6. Emollients, e.g. glycerol and sorbitols.
7. Preservatives, e.g. ascorbic acid and tocopherols.
8. Propellant (for aerosols), e.g. pentane and isobutane.

For additional ingredients that may be included in the shaving preparations of the present invention mention is made of the following citation that is incorporated herein by way of reference: Schubert, W. R. 1972. Shaving Preparations: Soaps, Creams, Oils and Lotions, Pg. 1–12. In M. S. Balsam and E. Sagrin eds. 2 Vols. *Cosmetics: Science and Technology*, Wiley Interscience, New York.

In practicing these aspects of the processes of this ivnention the procedure will vary somewhat depending on whether the $alpha_1$ agonist is contained in a pre-treatment composition or in the shaving composition. In the case of the former, the hair-bearing skin is first saturated with the pre-treatment composition for a period of from about 0.5 to about 3 minutes. If desired, the shaving operation is then carried out. However, in the ordinary case, the pre-treatment will be followed by the application of a conventional composition to the pre-treated hair-bearing skin, followed by the shaving operation.

In the case wherein the $alpha_1$ agonist is part of the shaving composition, the composition is applied to the hair-bearing skin in the conventional manner in sufficient quantity to cover all the hair. The shaving operation is then commenced.

The following examples are given to further illustrate the present invention. It is understood, however, that the invention is not limited thereto.

EXAMPLE 1

Pre-Shave Composition

| Ingredient | % by weight |
| --- | --- |
| Phenylephrine HCl | 1 |
| Ethyl Alcohol | 40 |
| Menthol | 0.1 |
| Camphor | 0.1 |
| Isopropyl Myristate | 18.8 |
| Rose Water Qs to 100 | |

The pre-treatment composition is applied to the face. After allowing 2 minutes for the active ingredient to cause the desired effect, a shave cream is applied over the pre-treatment. Shaving is then begun. An appropriate formulation could also be used prior to shaving with an electric razor.

EXAMPLE 2

Aerosol Shave Composition

| Ingredient | % by weight |
| --- | --- |
| Phenylephrine HCl | 1 |
| Ethyl Alcohol | 54 |
| Polyoxyethelene stearyl ether | 2 |
| Boric Acid | 1 |
| Hexachlorophene | 0.1 |
| Menthol | 0.1 |
| Musk Oil | 0.1 |
| Pentane | 10.0 |
| Water Qs to 100 | |

The shave cream formulation containing the phenylephrine is applied to the face. A 1 to 3 minute wait is allowed before shaving is started to permit the phenylephrine to cause the desired effects.

The compositions of this invention were evaluated by applying a solution of phenylephrine to one side of the face of a subject immediately prior to shaving. The pre-shave composition employed was 1% phenylephrine in deionized water. This was followed by the application of a conventional shaving composition followed by the actual shaving operation with a razor.

Shaving smoothness was evaluated subjectively by the shaved person as well as an independent judge; both of whom were blind as to the formulations of the compositions evaluated. Assessment was based upon perception of smoothness (touch), photographs and a credit card test reviewed periodically after shaving. With compositions of the present invention, we observed a closer shave and reduced bleeding from minor cuts/nicks. Also, the appearance of beard stubble was delayed as documented by photographs and the tape recorded credit card test.

As noted above, the prior art (Kortin and Rasp, Arzneimittel Forschung 4:63–66, 1954) indicates that the subcutaneous injection of phenylephrine into the forearm caused localized piloerection. As also noted above, the action of topically applied phenylephrine on facial pilomotor muscles was unexpected.

Phenylephrine is known to increase sweat output in isolated sweat glands. It was anticipated that injected phenylephrine would increase sweat in vivo. Studies were designed to compare the pharmacological effects of phenylephrine applied topically or subcutaneously. A rat foot pad model was used to detect increased sweat production. (Lansdown, J. Soc. Cosmetic. Chem. 24: 677–684, 1973.)

RESULTS: SUBCUTANEOUS INJECTION STUDY

Phenylephrine (0.5% or 1.0% solution) was injected (0.1 ml) into the foot pads of atropinized 120 μg/kg, s.c.) rats. Sweat output was evaluated fifteen minutes after phenylephrine injection. Compared to saline injection, phenylephrine (0.5% and 1.0% solutions) significantly increased sweat output (3.7 and 5.5-fold, respectively).

RESULTS: TOPICAL APPLICATION STUDY

The foot pads of atropinized rats (120 μg/kg, s.c.) were immersed in either 0.5% or 1.0% phenylephrine solutions for three minutes. Sweat output was evaluated fifteen minutes post-immersion. Phenylephrine did *not* increase sweat output in this test.

CONCLUSION

These result demonstrate that subcutaneously or topically applied phenylephrine does not have the same pharmacological effects. These rat foot pad data are supportive of the present contention because of the anatomical proximity of the sweat gland and pilomotor muscles. Both organs are in the dermis layer of the skin. On this basis, it is submitted that the prior art is not predictive of this invention.

What is claimed is:

1. A process for effecting a pilomotor response on hair-bearing skin which compromises applying topically to said hair-bearing skin area a pilomotor effective amount of an alpha$_1$ adrenergic receptor agonist which has essentially only alpha$_1$ adrenergic receptor agonist activity.

2. The process according to claim 1, wherein said alpha$_1$ adrenergic receptor agonist is contained in a shaving preparation.

3. The process according to claim 1, wherein said alpha$_1$ adrenergic receptor agonist is contained in a pre-shave preparation.

4. The process according to claim 1, wherein said alpha$_1$ adrenergic receptor agonist is contained in a depilatory wax composition.

5. The process according to claim 1, wherein said alpha$_1$ adrenergic receptor agonist is contained in a chemical depilatory composition.

6. The process according to claim 1, wherein said alpha$_1$ agrenergic receptor agonist is contained in a hair-bleach composition.

7. The process according to claim 1, wherein said alpha$_1$ adrenergic receptor agonist is contained in a hair dye composition.

8. In a shaving process involving the use of a razor to cut the hair off the hair-bearing portion of skin the improvement which comprises topically applying to said hair-bearing skin a composition containing an alpha$_1$ adrenergic receptor agonist which exhibits essentially only alpha$_1$ adrenergic receptor agonist activity and shaving the hair from said hair-bearing portion of skin, said composition containing said alpha$_1$ adrenergic receptor agonist in sufficient concentration to elicit a pilomotor response in said hair-bearing skin.

9. The process according to claim 8, wherein said the composition containing said alpha$_1$ adrenergic receptor agonist is a pretreatment composition.

10. The process according to claim 9, wherein the treatment of said hair-bearing skin with said pre-treatment composition is following by the application of a shaving composition to said hair-bearing skin.

11. The process according to claim 1, wherein said composition comprises a shaving composition containing said alpha$_1$ adrenergic receptor agonist.

12. The process according to claims 8, 9, 10, or 11, wherein said alpha$_1$ adrenergic receptor agonist is selected from the group consisting of phenylephrine and methoxamine.

13. The process according to claims 8, 9, 10 or 11, wherein said adrenergic alpha$_1$ receptor agonist is phenylephrine.

14. The process according to claims 8, 9, 10 or 11, wherein said alpha$_1$ adrenergic receptor agonist is present in said composition at a concentration in the range of from about 0.1% to about 10% by weight based on the total weight, of said composition.

15. The process according to claims 8, 9 10 or 11, wherein said alpha$_1$ adrenergic receptor agonist is present in said composition in a concentration of from about 0.2% to about 2% by weight, based on the total weight of said composition.

16. A shaving composition having incorporated therein at least one alpha$_1$ adrenergic receptor agonist which exhibits essentially only alpha$_1$ adrenergic receptor agonist activity, said alpha$_1$ adrenergic receptor agonist being present in sufficient concentration to elicit a pilomotor response when applied to topically to hair-bearing skin.

17. The composition according to claim 16, wherein said alpha$_1$ adrenergic receptor agonist is selected from the group consisting of phenylephrine and methoxamine.

18. The composition according to claim 16, wherein said alpha$_1$ adrenergic receptor agonist is phenylephrine.

19. The composition according to claims 16, 17 or 18, wherein said alpha$_1$ adrenergic receptor agonist is present in said composition in a concentration of from about 0.1% to about 10% by weight, based on the total weight of said composition.

20. The composition according to claims 16, 17 or 18, wherein said alpha$_1$ adrenergic receptor agonist is present in said composition at a concentration in the range of from about 0.2% to about 2% by weight, based on the total weight of said composition.

21. A pre-shave composition having incorporated therein at least one alpha$_1$ adrenergic receptor agonist which exhibits essentially only alpha$_1$ adrenergic receptor agonist activity, said alpha$_1$ adrenergic receptor agonist being present in sufficient concentration to elicit a pilomotor response when applied to hair-bearing skin.

22. The composition according to claim 21, wherein said alpha$_1$ adrenergic receptor agonist is selected from the group consisting of phenylephrine and methoxamine.

23. The composition according to claim 21, wherein said alpha$_1$ adrenergic receptor agonist is phenylephrine.

24. The composition according to claim 21, 22 or 23, wherein said alpha$_1$ adrenergic receptor agonist is present in said composition in the concentration of from about 0.1% to about 10% by weight, based on the total weight of said composition.

25. The composition according to claims 21, 22 or 23, wherein said alpha$_1$ adrenergic receptor agonist is present in said composition at a concentration in the range of from about 0.2% to about 2% by weight, based on the total weight of said composition.

* * * * *

UNITED STATES PATENT AND TRADEMARK OFFICE
CERTIFICATE OF CORRECTION

PATENT NO. : 4,853,216
DATED : August 1, 1989
INVENTOR(S) : Randy J. Koslo and Alison B. Lukacsko It is certified that error appears in the above-identified patent and that said Letters Patent is hereby corrected as shown below:

Column 2, line 33, after "it" insert -- is --.
Column 3, line 63, change "ivnention" to -- invention --.
Column 4, line 59, change ", judge" to -- judge, --.
Claim 1, at line 2, change "compromises" to -- comprises --
          at line 3, delete "area"
Claim 6, at line 2, change "agrenergic" to -- adrenergic --
Claim 11, at line 1, change "1" to -- 8 --
Claim 14, at line 5, after "weight" delete the comma
           at line 4, after "weight" and before "based" insert a comma
Claim 16, at line 6, after "applied" and before "topically" delete "to"

Signed and Sealed this

Twenty-sixth Day of June, 1990

*Attest:*

HARRY F. MANBECK, JR.

*Attesting Officer*   *Commissioner of Patents and Trademarks*